United States Patent [19]

Saurino

[11] 4,021,537

[45] May 3, 1977

[54] ORAL BACTERICIDAL COMPOSITIONS

[75] Inventor: Vincent R. Saurino, Boca Raton, Fla.

[73] Assignee: Research Lab Products, Inc., Boca Raton, Fla.

[22] Filed: Apr. 24, 1975

[21] Appl. No.: 571,398

Related U.S. Application Data

[63] Continuation of Ser. No. 386,875, Aug. 9, 1975, abandoned.

[52] U.S. Cl. .............................. 424/54; 424/288; 424/329
[51] Int. Cl.² .......................................... A61K 7/22
[58] Field of Search .............................. 424/49–58, 424/329

[56] References Cited

UNITED STATES PATENTS

| | | | |
|---|---|---|---|
| 3,282,776 | 11/1966 | Kitzke et al. | 424/329 |
| 3,525,793 | 8/1970 | Petrocci et al. | 424/329 |

FOREIGN PATENTS OR APPLICATIONS

| | | | |
|---|---|---|---|
| 1,226,821 | 3/1971 | United Kingdom | 424/50 |

*Primary Examiner*—Dolph H. Torrence
*Attorney, Agent, or Firm*—Cushman, Darby & Cushman

[57] ABSTRACT

Compositions for control of dental plaque comprising a synergistic mixture of an n-$C_{12-18}$ alkyl dimethyl benzyl ammonium halide, an n-$C_{12-14}$ alkyl dimethyl ethylbenzyl ammonium halide and a water-soluble or water dispersible ester of tributyl tin oxide.

38 Claims, No Drawings

ORAL BACTERICIDAL COMPOSITIONS

This is a continuation, of application Ser. No. 386,875 filed Aug. 9, 1975, now abandoned.

The present invention pertains to treatment and control of dental plaque by contacting, with human teeth, compositions containing active ingredients hereinafter defined which can be, for example, in the form of a mouthwash or tooth paste or tooth powder. The invention also is applicable to false teeth.

Dental caries is a disease which represents a significant health problem for which the principal therapy has been after-the-fact repair by filling cavities with metal, ceramic and/or plastic materials. Because of the prevalence of this disease, the amount of repair work required exceeds the capabilities of available qualified dental personnel. Therefore, for a long time, attempts have been made to determine how to control the problem of prevention of caries.

It has been recognized that caries are the result of biochemical attack on tooth enamel by substances present in the mouth. Therefore, one approach to the problem has been to harden dental enamel with fluoride, either by direct application or by incorporation of fluoride into drinking water. While the treatment, especially through drinking water, has been controversial it has been successful to a considerable extent.

The present invention relates to a different approach to the problem, that is to prevent the formation of the substances which attack tooth enamel. More specifically it relates to application of substances which reduce or prevent formation of dental plaque.

Although the matter is not entirely free of doubt, present theory indicates that caries result from the biochemical microenvironment established by microorganisms which attack enamel. These microorganisms are commonly present in the mouth. In particular, it is believed that the biochemical attack on enamel is the result of fermentation of carbohydrates by specific microorganisms including Lactobacillus, Acidophilus, Streptococci and perhaps a few other related microorganisms. These microorganisms are believed to constitute about half of the plaque material. Plaque appears as an amorphous-like substance which forms on the teeth of persons with poor hygiene and which ordinarily is removed by scaling.

In accordance to the present invention, plaque is controlled or eliminated by application to the teeth of various compositions of matter containing synergistic mixtures of quaternary ammonium compounds and other bactericidal compounds, as well as certain other non-bactericidal substances.

A preferred quaternary ammonium compound mixture contains two quaternary ammonium halide compounds (1) and (2) respectively, ordinarily in proportions of 5–95% of (1) to 95–5% of (2), preferably 30–80% of (1) with 70–20% of (2), and especially a 50—50 mixture, the above proportions and those following being by weight. Compound (1) is an alkyl-dimethyl-benzyl-ammonium chloride and compound (2) is an alkyl-dimethyl-ethylbenzyl-ammonium chloride.

The following are particularly suitable as compounds (1) and (2): (1) n-alkyl (60% $C_{14}$, 30% $C_{16}$, 5% $C_{12}$, 5% $C_{18}$)-dimethyl-benzyl-ammonium chloride, and (2) n-alkyl (68% $C_{12}$, 32% $C_{14}$)-dimethyl-ethylbenzyl-ammonium chloride. As indicated above, compounds (1) and (2) can be admixed with various proportions such that one of said compounds is present in amounts of from 5% to 95% and the other compound making up the balance and preferably they can be present in amounts of 30–80% of (1) and 70–20% of (2) or still more preferred is when compounds (1) and (2) are present in essentially equal amounts.

As indicated above, it is preferred to include in the compositions other bactericidal components, such as cetylpyridinium-chloride and especially water-soluble and/or waterdispersable esters of bis(tri-n-butyltin)oxide, as well as tributyl tin salts.

Among the water-soluble and/or water dispersable esters of bis(tri-n-butyltin)oxide, tri-n-butyltin benzoate has been found to be particularly useful. However, other water-soluble and/or water-dispersable esters with organic aliphatic and aromatic acids may be used, particularly with lower saturated aliphatic and monocarbocyclic aromatic monocarboxylic acids, for example tri-n-butyltin salicylate, bis(tri-n-butyltin)-silicofluoride, tri-n-butyltin-butyrate, and others. When these tin compounds are used, a wide range of proportions relative to the aforesaid mixture of compounds 1 and 2 may be used, generally in the range equal parts of the quaternary salt mixture and the tin compound to 200 parts of the quaternary salt to one part of tin compound.

Wetting agents which may be used include compatible cationic, nonionic, and/or anionic surfactants. Particularly useful materials include octyl-phenoxy-polyethoxy-ethanol and cetyl pyridinium chloride. The latter is advantageous in increasing the cleaning power of the composition while the former enhances penetration and spreading.

Other additives include flavoring materials such as methyl salicylate and ordinary food flavorings, sweetening materials such as sorbitol and veratraldehyde, thickening agents such as gelatin and thixotropic materials. In tooth paste and in tooth powder formulations formulations, various abrasive agents may be used.

The following examples of formulations illustrate some combinations which have been prepared according to the invention:

| | | | | | | | | | | | | |
|---|---|---|---|---|---|---|---|---|---|---|---|---|
| | | | | | Constituents Other Than Water in Percentage by Weight of Solution, the Balance Being Water | | | | | | | |
| Formula No. | 50:50* Mixture of Compounds (1) and (2) | Tributyl Tin Benzoate | Cetyl Pyridinium Chloride | Isopropanol | Octyl Phenoxy Polyethoxy Ethanol (Triton X-100) | Sorbitol | Food Flavoring | Methyl Salicylate | Veratraldehyde | Gelatin | Jaquat A-20-A | Sodium Borite |
| 1 | | | 10 | | | | | | | | | |
| 2 | 2.5 | | 5 | | 5 | | | | | | | |
| 3 | 2.5 | | 2.5 | | 5 | | .2 | | | | | |
| 4 | 23.45 | .5 | 8.76 | | 5 | | .1 | .25 | .15 | | | |
| 5 | 2.5 | 2.52 | | 5 | 10 | 10 | .32 | | | | | |

-continued

| Formula No. | 50:50* Mixture of Compounds (1) and (2) | Tributyl Tin Benzoate | Cetyl Pyridinium Chloride | Isopropanol | Octyl Phenoxy Polyethoxy Ethanol (Triton X-100) | Sorbitol | Food Flavoring | Methyl Salicylate | Veratraldehyde | Gelatin | Jaquat A-20-A | Sodium Borite |
|---|---|---|---|---|---|---|---|---|---|---|---|---|
| 6 | 0.1425 | | 0.1425 | | .0285 | 10.13 | 0.3114 | | | | 2.5 | .035 |
| 7 | .003 | | .003 | | .036 | 11.2 | .03024 | | | 2.5 | | |
| 8 | .0425 | | .0425 | | 5.85 | 10 | .0034 | | | | 2.8 | .035 |
| 9 | .08442 | .00180 | .031536 | | .018 | 11.2 | .30036 | .0009 | .00054 | 2.2 | | |
| 10 | .0335 | | .0335 | | .067 | 11.2 | .30268 | | | 2.2 | | |
| 11 | .072695 | .00155 | .027156 | | .0155 | 11.2 | .30031 | .000775 | .000465 | 2.2 | | |
| 12 | 5.8625 | .5 | .554 | | 9.9 | 10 | .4 | | | | | |
| 13 | 2.4475 | 2.53 | 1.6277 | | 9.61 | 19.58 | .6 | | | | | |

*Compound (1): n-alkyl(60% $C_{14}$, 30% $C_{16}$, 5% $C_{12}$, 5% $C_{18}$) dimethyl benzyl ammonium chloride
Compound (2): n-alkyl (68% $C_{12}$, 32% $C_{14}$) dimethyl ethylbenzyl ammonium chloride Bacterial activity of formula 4 diluted 1:50 with sterile water was determined as follows:

BACTERICIDAL ACTIVITY

I. Method: Methods of Analyses, AOAC, 11th ed., 1970, pg. 61, Use-Dilution Method Staphylococcus aureus ATCC No. 6538 Salmonella choleraesuis ATCC No. 10708 Pseudomonas aeruginosa PRDIO No. (ATCC No. 15442) Rothia dentocariosus ATCC No. 17931 Lactobacillus casei These values were determined at 95% confidence level over replicate testing. A minimum performance of 59/60 negative carrier subcultures was required. The results in each case were as follows:

TABLE I

I. Bactericidal Study (after 48 hrs. incubation at 37° C.)

| Tube Series | 1 | 2 | 3 | 4 | 5 | 6 | 7 | 8 | 9 | 10 | Control | % Kill |
|---|---|---|---|---|---|---|---|---|---|---|---|---|
| Formula 4 | − | − | − | − | − | − | − | − | − | − | + | 100% |

(+) Growth (−) No Growth (PC) Precipitate Cloud-Made

II. Bacteriostatic Study (after 48 hrs. incubation at 37° C.) Transfer of negative carriers to sterile medium.

| Tube Series | 1 | 2 | 3 | 4 | 5 | 6 | 7 | 8 | 9 | 10 | Control | % Kill |
|---|---|---|---|---|---|---|---|---|---|---|---|---|
| Formula 4 | − | − | − | − | − | − | − | − | − | − | + | 100% |

Reinoculation of negative tubes with same organism, with 4 mm loop (after 48 hrs. incubation at 37° C.).

| Tube Series | 1 | 2 | 3 | 4 | 5 | 6 | 7 | 8 | 9 | 10 | Control | % Kill |
|---|---|---|---|---|---|---|---|---|---|---|---|---|
| Component A-500 | + | + | + | + | + | + | + | + | + | + | | |

Results indicating synergistic activity among the various active ingredients were observed with formulations varying in the number and/or concentrations of these active ingredients. The following table illustrates this reaction when the first six formulations from the previous table, representing variations in both numbers and concentrations of active ingredients, are evaluated for percentage of kill against the test organisms:

TABLE II

| | | Organism | | | | |
|---|---|---|---|---|---|---|
| Formula No. | Dilution | S. aureus ATCC No. 6538 | S.choleraesuis ATCC No. 10708 | P.aeruginosa ATCC No. 15442 | Rothia dentocariosus ATCC No. 17931 | Lactobacillus casei |
| 1 | 1:100 | 80% | 80% | 40% | 30% | 20% |
| 2 | 1:50 | 90% | 80% | 60% | 90% | 100% |
| 3 | 1:50 | 90% | 80% | 80% | 90% | 100% |
| 4 | 1:350 | 100% | 100% | 100% | 100% | 100% |
| 5 | 1:350 | 100% | 100% | 100% | 100% | 100% |
| 6 | 1:350 | 90% | 60% | 30% | 90% | 80% |

In the zone of inhibition test, a 1 cm diameter spot was placed on a nutrient medium seeded with the specific organism as indicated. After 24 hours of incubation at 37° C., the diameter of the zone free from growth was recorded in millimeters.

TABLE III

| | | Organism | | | |
|---|---|---|---|---|---|
| Formula No. | S. aureus ATCC No. 6538 | S. choleraesuis ATCC No. 10708 | P. aeruginosa ATCC No. 15442 | Rothia dentocariosus ATCC NO. 17931 | Lactobacillus Casei |
| 6 | 5mm | 7mm | 2mm | 6mm | 6mm |
| 7 | 11mm | 8mm | 3mm | 15mm | 15mm |
| 8 | 12mm | 8mm | 3mm | 16mm | 16mm |

TABLE III-continued

| Formula No. | S. aureus ATCC No. 6538 | S. choleraesuis ATCC No. 10708 | P. aeruginosa ATCC No. 15442 | Rothia dentocariosus ATCC NO. 17931 | Lactobacillus Casei |
|---|---|---|---|---|---|
| 9 | 4mm | 3mm | 1mm | 5mm | 5mm |
| 10 | 6mm | 4mm | 1mm | 8mm | 7mm |
| 11 | 10mm | 8mm | 3mm | 15mm | 16mm |

Residual time studies were carried out on Formula 4, using S. aureus ATCC No. 6538 and R. dentocariosus ATCC No. 17931. The residual time study includes dipping approximately 40 glass slides in the formulations for a few minutes to insure total wetting of each slide's surface, then removing the slides, permitting them to air dry and storing them in a dust-free box for daily testing. Each day a 24-hour culture of a designated organism is used to spread a 4 ml. loopful over one of the treated slides in an area of approximately ⅞ inch. The respective organisms are permitted to remain in contact with the slides for 10 minutes. The slide is then washed in a jar containing 40 ml. of recovery medium and finally it is transferred into a second jar containing the same medium; the slide is left to stand in the second jar until final results are determined. Although all of the slides were treated only the initial time, one of the slides so treated is used each day without any further treatment. Thus the test provides an estimate of the residual capacity of the formulations. The results are shown in Table IV.

TABLE IV

| Date | S. aureus 1st | S. aureus 2nd | R. dentocariosus 1st | R. dentocariosus 2nd |
|---|---|---|---|---|
| 12/6 | — (contam.) | — | — | — |
| 12/7 | — | — | — | — |
| 12/8 | — | — (contam.) | — (contam.) | — |
| 12/9 | — | — | — | — |
| 12/10 | — | — | — | — |
| 12/11 | — | — ppt | — | — |
| 12/12 | — | — | — | — |
| 12/13 | — (contam.) | — | — | — |
| 12/14 | — | — | — | — |
| 12/15 | — | — | — | — |
| 12/16 | — | — | — (contam.) | — |
| 12/18 | — | — | — | — |
| 12/19 | — | — (contam.) | — | — |
| 12/20 | — | — | — | + ppt |
| 12/22 | — | — | + ppt | + ppt |
| 12/26 | — | — | + ppt | + ppt |
| 12/28 | — | + ppt | + ppt | + heavy ppt |
| 12/30 | — | + ppt | + ppt | + heavy ppt |

+ = Growth
Tubes with ppt when recultured showed viable organisms, however no additional growth in original tube.
Letheen Broth used.

The active ingredients may be mixed with suitable flavoring materials and other components. For example, they may be mixed with conventional tooth paste formulations or dissolved in water for use in a mouthwash. They may then be applied to teeth during brushing or rinsing. The same formulations may be used to cleanse dentures. It will be appreciated that in normal use, the composition may come into contact with mucosa tissues of the nasal pharanx, particularly if gargling is practiced along with rinsing. Therefore, the composition may simultaneously destroy common cold and related organisms on those tissues.

The composition of this invention relates to that described in my patent application Ser. No. 317,225, filed Dec. 21, 1972, now abandoned, which relates to creating a barrier against transmission of venereal infections. The compositions of the present invention are useful for the same purpose; in addition those containing the aforesaid tin compound are more effective in treating other vaginal infections.

I claim:

1. A method of removing dental plaque from teeth which comprises contacting said teeth with a composition of matter comprising (a) a synergistic mixture of a quaternary ammonium compound (1) and a quaternary ammonium compound (2), said compound (1) being an n-alkyl (5% $C_{12}$, 60% $C_{14}$, 30% $C_{16}$, 5% $C_{18}$) dimethyl benzyl ammonium chloride and said compound (2) being n-alkyl (68% $C_{12}$, 32% $C_{14}$)-dimethylethylbenzyl ammonium chloride, the proportions of said compounds (1) and (2) being in the range of 5% to 95% of compound (1) and 95% to 5% of compound (2) and (b) a water soluble or water dispersable ester of bis(tri-n-butyltin) oxide, the said composition of matter containing about 1 to 200 parts by weight of said synergistic mixture (a) for each part by weight of said ester of tributyl tin oxide.

2. A method as set forth in claim 1 in which the proportions of said compounds (1) and (2) are in the range of 30 to 80% of compound (1) and 70–20% of compound (2).

3. A method as set forth in claim 1 in which the proportions of compounds (1) and (2) are approximately equal.

4. A method as set forth in claim 1 in which said ester is tributyl tin benzoate.

5. A method as set forth in claim 4 in which the composition of matter contains about 1 to 50 parts by weight of said synergistic mixture for each part by weight of tributyl tin benzoate.

6. A method as set forth in claim 1 in which said composition also contains a surface active agent.

7. A method as set forth in claim 6 in which the surface active agent is at least one member of the group consisting of cationic and nonionic surface active agents.

8. A method as set forth in claim 7 in which the composition contains cetyl pyridinium chloride and octyl phenoxy polyethoxy ethanol.

9. A method as set forth in claim 1 in which said composition of matter comprises about 1–50 parts by weight of a mixture of equal amounts by weight of n-alkyl (5% $C_{12}$, 60% $C_{14}$, 30% $C_{16}$, 5% $C_{18}$) dimethyl benzyl ammonium chloride and n-alkyl (68% $C_{12}$, 32% $C_{14}$)-dimethyl-ethylbenzyl ammonium chloride, and 1 part by weight of tributyl tin benzoate, cetyl pyridinium chloride and octyl phenoxy polyethoxy ethanol.

10. A method of preventing the formation of dental plaque on teeth which comprises contacting said teeth with a composition of matter comprising (a) a synergistic mixture of a quaternary ammonium compound (1)

and a quaternary ammonium compound (2), said compound (1) being an n-$C_{12-18}$ alkyl, dimethyl, benzyl ammonium halide and said compound (2) being an n-$C_{12-14}$ alkyl dimethyl ethylbenzyl ammonium halide and (b) a water-soluble or water dispersible ester of bis(tri-n-butyltin)oxide.

11. A method as set forth in claim 10 in which said compound (1) is n-alkyl (5% $C_{12}$, 60% $C_{14}$, 30% $C_{16}$, 5% $C_{18}$) dimethyl benzyl ammonium chloride and said compound (2) is n-alkyl (68% $C_{12}$, 32% $C_{14}$)-dimethyl-ethylbenzyl ammonium chloride.

12. A method as set forth in claim 10 in which the proportions of said compounds (1) and (2) are in the range 5% to 95% of compound (1) and 95% to 5% of compound (2).

13. A method as set forth in claim 12 in which the proportions of said compounds (1) and (2) are in the range of 30 to 80% of compound (1) and 70–20% of compound (2).

14. A method as set forth in claim 12 in which the proportions of compounds (1) and (2) are approximately equal.

15. A method as set forth in claim 10 in which said composition of matter contains a water-soluble or water dispersible ester of tributyl tin oxide.

16. A method as set forth in claim 15 in which said ester is tributyl tin benzoate.

17. A method as set forth in claim 16 in which the composition of matter contains about 1 to 200 parts by weight of said synergistic mixture for each part by weight of tributyl tin benzoate.

18. A method as set forth in claim 17 in which the composition of matter contains about 1 to 50 parts by weight of said synergistic mixture for each part by weight of tributyl tin benzoate.

19. A method as set forth in claim 10 in which said composition also contains a surface active agent.

20. A method as set forth in claim 19 in which the surface active agent is at least one member of the group consisting of cationic and nonionic surface active agents.

21. A method as set forth in claim 20 in which the composition contains cetyl pyridinium chloride and octyl phenoxy polyethoxy ethanol.

22. A method as set forth in claim 10 in which said composition of matter comprises about 1–50 parts by weight of a mixture of equal amounts by weight of n-alkyl (5% $C_{12}$, 60% $C_{14}$, 30% $C_{16}$, 5% $C_{18}$) dimethyl benzyl ammonium chloride and n-alkyl (68% $C_{12}$, 32% $C_{14}$)-dimethyl-ethylbenzyl ammonium chloride, and 1 part by weight of tributyl tin benzoate, cetyl pyridinium chloride and octyl phenoxy polyethoxy ethanol.

23. A composition of matter for removing dental plaque from teeth and preventing formation of plaque on teeth comprising (a) a synergistic mixture of a quaternary ammonium compound (1) and a quaternary ammonium compound (2), said compound (1) being an n-$C_{12-18}$ alkyl, dimethyl benzyl ammonium halide and said compound (2) being an n-$C_{12-14}$ alkyl dimethyl ethylbenzyl ammonium halide and (b) a water-soluble or water-dispersible ester of bis(tri-n-butyltin) oxide.

24. A composition as set forth in claim 23 in which said compound (1) is an n-alkyl (5% $C_{12}$, 60% $C_{14}$, 30% $C_{16}$, 5% $C_{18}$) dimethyl benzyl ammonium chloride and said compound (2) is an n-alkyl (68% $C_{12}$, 32% $C_{14}$) dimethyl ethylbenzyl ammonium chloride.

25. A composition as set forth in claim 24 in which the proportions of said compounds (1) and (2) are in the range 5% to 95% of compound (1) and 95% to 5% of compound (2).

26. A composition as set forth in claim 25 in which the proportions of said compounds (1) and (2) are in the range of 30 to 80% of compound (1) and 70 to 20% of compound (2).

27. A composition as set forth in claim 26 in which the proportions of compounds (1) and (2) are approximately equal.

28. A composition as set forth in claim 23 in which said ester is tributyl tin benzoate.

29. A composition as set forth in claim 23 which also contains a surface active agent.

30. A composition as set forth in claim 29 in which the surface active agent is at least one member of the group consisting of cationic and nonionic surface active agents.

31. A composition as set forth in claim 29 in which the composition contains cetyl pyridinium chloride and octyl phenoxy polyethoxy ethanol.

32. A composition as set forth in claim 23 which comprises about 1–50 parts by weight of a mixture of equal amounts by weight of n-alkyl (5% $C_{12}$, 60% $C_{14}$, 30% $C_{16}$, 5% $C_{18}$) dimethyl benzyl ammonium chloride and n-alkyl (68% $C_{12}$, 32% $C_{14}$) dimethyl ethylbenzyl ammonium chloride, and 1 part by weight of tributyl tin benzoate, cetyl pyridinium chloride and octyl phenoxy polyethoxy ethanol.

33. A composition as set forth in claim 32 in which the ratio of the proportion of tributyl tin benzoate to cetyl pyridinium chloride is in the range 0.50 to 8.75.

34. A composition as set forth in claim 32 in which the ratio of the proportions of tributyl tin benzoate to cetyl pyridinium chloride is 0.20 to 1.0.

35. A composition as set forth in claim 23 in which the ratio of the proportions by weight of compounds (1) and (2) is 10 to 13.

36. A composition as set forth in claim 32 in which the ratio of the proportions by weight of cetyl pyridinium chloride to compound (2) is 8.75 to 11.73.

37. A composition as set forth in claim 36 wherein the ratio is 6 to 10.

38. A composition as set forth in claim 32 containing also isopropyl alcohol.

* * * * *